United States Patent [19]

Pasque

[11] Patent Number: 5,290,227
[45] Date of Patent: Mar. 1, 1994

[54] METHOD OF IMPLANTING BLOOD PUMP IN ASCENDING AORTA OR MAIN PULMONARY ARTERY

[76] Inventor: Michael K. Pasque, 13218 Hawkshead Ct., Town and Country, Mo. 63131

[21] Appl. No.: 35,788
[22] Filed: Mar. 23, 1993

Related U.S. Application Data

[63] Continuation-in-part of Ser. No. 926,779, Aug. 6, 1992, abandoned.

[51] Int. Cl.$^5$ .................................................. A61M 1/03
[52] U.S. Cl. ............................ 600/16; 417/356; 623/3
[58] Field of Search .............. 600/16, 17; 417/356; 623/3

[56] References Cited

U.S. PATENT DOCUMENTS

| | | | |
|---|---|---|---|
| 2,500,400 | 3/1950 | Cogswell | 417/356 X |
| 3,842,440 | 10/1974 | Karlson | 3/1 |
| 4,210,409 | 7/1980 | Child | 417/241 |
| 4,688,998 | 8/1987 | Olsen | 417/356 |
| 4,779,614 | 10/1988 | Moise | 600/16 |
| 4,908,012 | 3/1990 | Moise et al. | 600/16 |
| 4,919,647 | 4/1990 | Nash | 600/16 |
| 4,957,504 | 9/1990 | Chardack | 417/356 X |
| 4,994,078 | 2/1991 | Jarvik | 623/3 |
| 4,995,857 | 2/1991 | Arnold | 623/3 X |
| 5,089,017 | 2/1992 | Young et al. | 623/3 |
| 5,112,200 | 5/1992 | Isaacson et al. | 417/356 |

OTHER PUBLICATIONS

Mitamura, Y., et al, "The Valvo–Pump: An axial, non-pulsatile blood pump," *Amer. Soc. Artif. Int. Organs Transactions 37:* M510-M512 (1991).

Qian, K. X., et al, "Toward an implantable impeller total heart," *Trans. Am. Soc. Artif. Intern. Organs 33:* 704-707 (1987).

Qian, K. X., et al, "The realization of pulsatile implantable impeller pump with low hemolysis," *Artif. Organs 13:* 162-169 (1989).

Qian, K. X., "Experience in Reducing the Hemolysis of an Impeller Assist Heart," *Trans. Am. Soc. Artif. Intern. Organs 35:* 46-53 (1989).

Qian, K. X., "Haemodynamic approach to reducing thrombosis and haemolysis in an impeller pump," *J. Biomed. Engr. 12:* 533-535 (1990a).

Qian, K. X., "New investigations of a pulsatile impeller blood pump," *Trans. Am. Soc. Artif. Intern. Organs 36:* 33-35 (1990b).

*Primary Examiner*—Richard E. Gluck
*Attorney, Agent, or Firm*—Patrick D. Kelly

[57] ABSTRACT

This invention relates to a method of surgically implanting a blood pump into the ascending aorta or pulmonary artery of a patient with a diseased or damaged heart ventricle. One preferred type of pump which is well-suited for such implantation has an impeller design that generates central axial flow (CAF). After implantation of the CAF pump, blood flows through the hollowed-out rotor shaft of an electric motor. The CAF rotor shaft contains angled vanes mounted on the inner surface of the hollow shaft, extending only part of the distance toward an imaginary axis at the center of the rotor shaft. Rotation of the hollow shaft with its angled vanes pumps blood through the pumping unit. The vanes contact and impart forward motion to a portion of the blood at the periphery of the flow path, generating an outer fluid annulus which is being directly propelled by the vanes. Blood cells near the center of the cylinder are not touched by the vanes as they pass through the pump; instead, they are drawn forward by viscous flow of the surrounding annulus. In the method of this invention, the pump and motor unit is inserted downstream of an aortic or pulmonary valve which is left intact and functioning, by means such as suturing the arterial walls to short attachment cuffs at each end of the pump. After insertion, the pump lies directly in line with the artery, so that directional changes, shear forces, and artificial surfaces contacted by blood are all minimized. Unlike shunt systems, placement entirely within an aorta or pulmonary artery can provide pulsatile flow if desired, and can reduce the pressure that a damaged or diseased ventricle must pump against. In addition, the placement and design of the CAF pump allow maximal use of the residual functioning of the patient's heart and will not lead to catastrophic backflow if the pump suffers a power or mechanical failure.

14 Claims, 3 Drawing Sheets

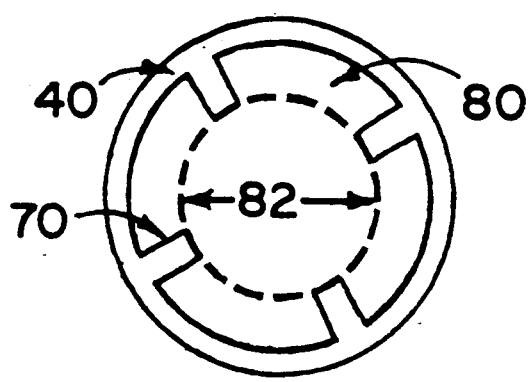
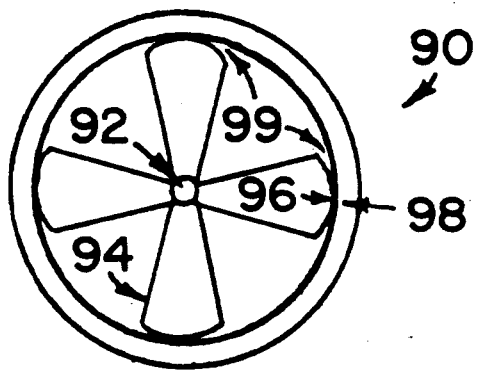
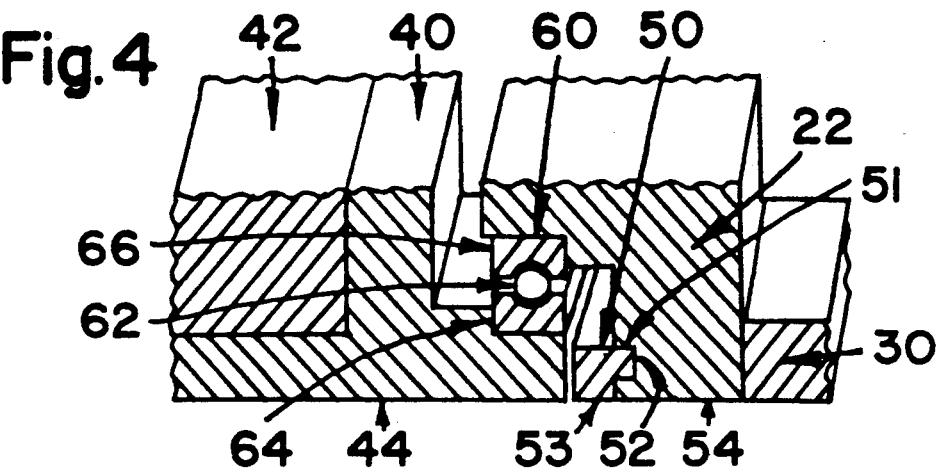
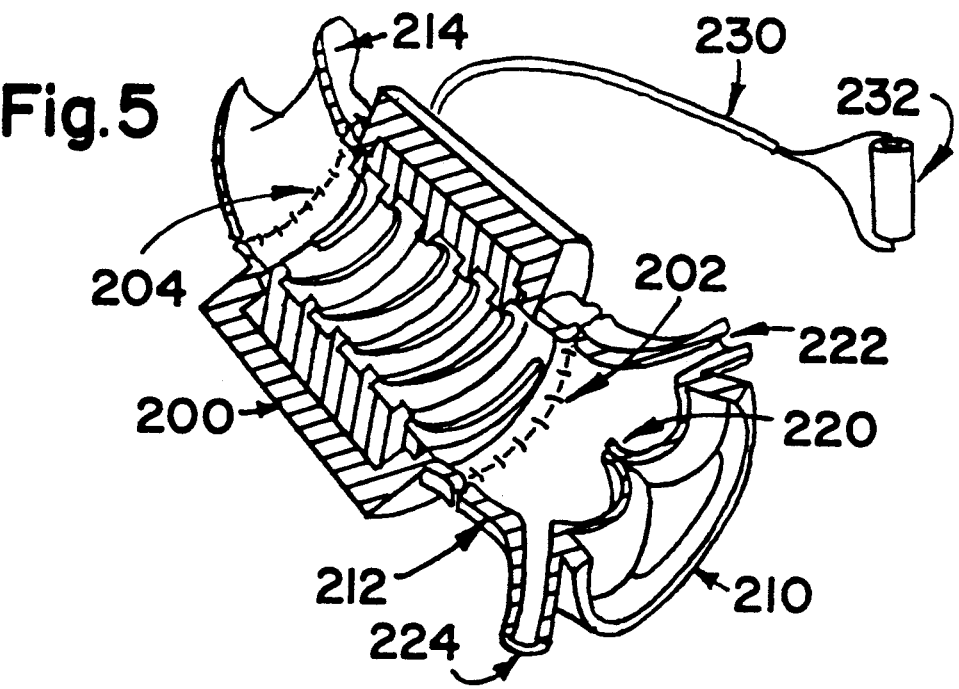

METHOD OF IMPLANTING BLOOD PUMP IN ASCENDING AORTA OR MAIN PULMONARY ARTERY

RELATED APPLICATION

This is a continuation-in-part of U.S. application Ser. No. 07/926,779, filed on Aug. 6, 1992 now abandoned.

BACKGROUND OF THE INVENTION

This invention is in the field of surgically implantable blood pumps that can be used to augment or replace the pumping action of the heart.

Several types of surgically implantable pumps have been developed in an effort to provide mechanical means for augmenting or replacing the pumping action of damaged or diseased hearts. Some of these pumps are designed to support single ventricular function. Such pumps usually support the left ventricle, which supplies the entire body except the lungs, since it becomes diseased far more commonly than the right ventricle, which supplies only the lungs. Other devices have been tested and used for providing biventricular function. As used herein, "testing" refers to tests on animals (such as dogs or cows), while "use" refers to implantation in humans.

Depending on the needs of a particular patient and the design of a pump, pumping units such as so-called "LVAD's" (left ventricular assist devices) can be implanted to assist a functioning heart that does not have fully adequate capacity. Other types of pumps, such as the so-called "Jarvik heart," can be used to completely replace a heart which has been surgically removed.

Temporary as well as permanent implantable pumps have been developed. "Permanent" in this sense refers to the remaining life of the patient; after a patient's death, any artificial pumping device is usually removed for analysis. "Temporary" implantation usually involves (1) an attempt to reduce the stress on a heart while it recovers from surgery or some other short term problem, or (2) use of a pump as a "bridge" to forestall the death of a patient until a suitable donor can be found for cardiac transplantation.

Throughout the remainder of this application, the term "blood pump" or "pump" refers to, and is limited to, surgically implantable pumps. Such pumps do not include pumps which remain outside the body of a patient. For example, the pump in a conventional cardiopulmonary bypass machine, used during most types of heart surgery, would not be covered by the specification or claims herein. For convenience, all references to "aorta" refer to the ascending aorta. The descending portion of the aorta, which passes through the trunk and abdomen, is not relevant to this invention.

The most widely tested and commonly used implantable blood pumps employ variable forms of flexible sacks (also spelled sacs) or diaphragms which are squeezed and released in a cyclical manner to cause pulsatile ejection of blood. Such pumps are discussed in books or articles such as Hogness and Antwerp 1991, DeVries et al 1984, and Farrar et al 1988, and in U.S. Pat. Nos. 4,994,078 (Jarvik 1991), 4,704,120 (Slonina 1987), 4,936,758 (Coble 1990), and 4,969,864 (Schwarzmann et al 1990). Sack or diaphragm pumps are mechanically and functionally quite different from the present invention.

An entirely different class of implantable blood pumps uses rotary pumping mechanisms. Most rotary pumps can be classified into two categories: centrifugal pumps, and axial pumps. Centrifugal pumps, which include pumps marketed by Sarns (a subsidiary of the 3M Company) and Biomedicus (a subsidiary of Medtronic, Eden Prairie, Minn.), direct blood into a chamber, against a spinning interior wall (which is a smooth disk in the Medtronic pump). A flow channel is provided so that the centrifugal force exerted on the blood generates flow.

By contrast, axial pumps provide blood flow along a cylindrical axis, which is in a straight (or nearly straight) line with the direction of the inflow and outflow. Depending on the pumping mechanism used inside an axial pump, this can in some cases reduce the shearing effects of the rapid acceleration and deceleration forces generated in centrifugal pumps. However, the mechanisms used by axial pumps can inflict other types of stress and damage on blood cells.

Some types of axial rotary pumps use impeller blades mounted on a center axle, which is mounted inside a tubular conduit. As the blade assembly spins, it functions like a fan, or an outboard motor propeller. As used herein, "impeller" refers to angled vanes (also called blades) which are constrained inside a flow conduit; an impeller imparts force to a fluid that flows through the conduit which encloses the impeller. By contrast, "propeller" usually refers to non-enclosed devices, which typically are used to propel vehicles such as boats or airplanes.

Another type of axial blood pump, called the "Haemopump" (sold by Nimbus) uses a screw-type impeller with a classic screw (also called an Archimedes screw; also called a helifoil, due to its helical shape and thin cross-section). Instead of using several relatively small vanes, the Haemopump screw-type impeller contains a single elongated helix, comparable to an auger used for drilling or digging holes. In screw-type axial pumps, the screw spins at very high speed (up to about 10,000 rpm). The entire Haemopump unit is usually less than a centimeter in diameter. The pump can be passed through a peripheral artery into the aorta, through the aortic valve, and into the left ventricle. It is powered by an external motor and drive unit.

Centrifugal or axial pumps are commonly used in three situations: (1) for brief support during cardiopulmonary operations, (2) for short-term support while awaiting recovery of the heart from surgery, or (3) as a bridge to keep a patient alive while awaiting heart transplantation. However, rotary pumps generally are not well tolerated for any prolonged period. Patients who must rely on these units for a substantial length of time often suffer from strokes, renal (kidney) failure, and other organ dysfunction. In addition, rotary devices, which usually must operate at relatively high speeds, may impose high levels of turbulent and laminar shear forces on blood cells. These forces can damage or lyse (break apart) red blood cells. A low blood count (anemia) may result, and the disgorged contents of lysed blood cells (which include large quantities of hemoglobin) can cause renal failure.

One of the most important problems in axial rotary pumps in the prior art involves the gaps that exist between the outer edges of the blades, and the walls of the flow conduit (see FIG. 3-B). These gaps are the site of severe turbulence and shear stresses, due to two factors. Since implantable axial pumps operate at very high speed, the outer edges of the blades move extremely fast and generate high levels of shear and turbulence. In addition, the gap between the blades and the wall is usually kept as small as possible, to increase pumping efficiency and to reduce the number of cells that become entrained in the gap area. This can lead to high-speed compression of blood cells as they are caught in a narrow gap between the stationary interior wall of the conduit, and the rapidly moving tips or edges of the blades.

In order to reduce turbulence and shear around the outer edges of the blades, and to strengthen and reinforce the blades, large pumping units used for pumping oil or water often use a circular rim attached to the outer edges of the blades. However, to the best of the Applicant's knowledge, such rims are not used in axial blood pumps, since such rims would increase laminar shear between the rotating rim and stationary cylinder walls, and would also contribute to stasis between the two surfaces.

Despite their disadvantages, axial pumping devices remain of great interest, since they are smaller and less complex than sack or diaphragm pumps. Axial pumps do not need inlet or outlet valves, they have fewer and smaller blood-contacting surfaces, and they can be surgically implanted much more easily than sack or diaphragm pumps.

The CAF Pump (A Preferred Embodiment)

Before certain items of prior art can be understood in proper context, a specific type of pump which provides a preferred embodiment for use in the method of this invention must be briefly described. This pump, referred to herein as a "central axial flow" (CAF) pump, is a rotary pump which belongs in the axial flow (rather than centrifugal force) subclass. The CAF pump consists of a completely enclosed electric motor with a stator housing and rotor. The impeller is different from that seen in most other axial pumps, since it has a tubular hollowed-out rotor shaft. The vanes of the impeller are spaced around the inside surface of the hollowed-out rotor shaft. The vanes extend inwardly from the tube walls, toward the center axis of the rotor shaft; however, they span only part of the distance between the outer walls and center of the rotor shaft. This leaves an open region in the center of the rotor shaft. During use, blood flows through the open region that passes through the center of the rotor shaft (hence the name, "central axial flow"). The vanes directly contact and impart forward motion to the blood in an annular region, located around the outside of the tubular passageway. The blood near the center of the tubular rotor is not touched by the vanes as it passes through the pump; instead, it is drawn and propelled forward by viscous fluid forces.

In addition, this invention also discloses, apparently for the first time, a new method of surgically implanting a pump (including, but not limited, a CAF pump as described herein) directly into an aorta or pulmonary artery, which can be called ventricular outflow arteries since they receive blood directly from the ventricular chambers of a heart. In one preferred method of implantation, an aorta or pulmonary artery is transsected (i.e., cut in a manner which crosses the main axis of the artery) downstream of the aortic or pulmonary valve. The two exposed ends of the transsected arterial wall are attached around the entire periphery of the pump inlet and outlet, by means such as suturing the arterial ends to attachment devices such as Dacron suture cuffs that are attached to the inlet and outlet ends of the pump. Thereafter, all blood pumped out of a ventricle and through the aortic or pulmonary valve passes through the pump, with the minor exception of blood which immediately leaves the aorta and travels through the coronary arteries before entering an aortic pump. The pump imparts additional pumping force to the ejected blood, to augment (or in some situations entirely replace) the pumping activity of the damaged or diseased ventricle.

As described in more detail below, this method of implanting a pump directly in the flow path of an aorta or pulmonay artery can be used to provide pulsatile flow. This is a potentially important advantage, and most shunt pumps and other rotary pumps apparently cannot accomplish this objective, for reasons described below.

The Shunt Pumps of Arnold and Olsen

Pumps which use peripherally-mounted vanes with central axial flow paths have been described for various uses, ostensibly including blood pumping (although, to the best of the Applicant's knowledge, no such pumps have ever been sold or used for actual pumping of blood in humans).

U.S. Pat. No. 2,500,400 (Cogswell, 1950) discloses a pump with peripherally mounted vanes and central axial flow, developed for automobile engines. U.S. Pat. No. 4,688,998 (Olsen et al 1987) discloses a similar peripheral vane arrangement intended for a surgically implantable shunt pump (see FIG. 3 and Column 7 of the '998 patent). U.S. Pat. No. 4,995,857 (Arnold, 1991) describes a somewhat similar system which uses a single large helifoil blade that stretches the length of the pump. Arnold's helifoil impeller is somewhat similar to a Nimbus "Haemopump" helifoil; however, the Nimbus helifoil is mounted on a center axle with the vane extending outwardly, while the Arnold helifoil is affixed along its outer edge to the interior wall of a rotating cylinder, with a relatively narrow open flow path in the center of the helifoil.

The Arnold and the Olsen et al patents both describe shunt pumps, which are implanted in a manner entirely different from the method described herein. However, these pumps are discussed in some detail below, since (1) their internal structures are somewhat similar to the CAF peripheral vane embodiment described herein, and, (2) the differences between shunt implantation, used by Olsen et al and Arnold, and arterial implantation, described herein, help to illustrate certain advantages of the subject invention.

The Arnold and Olsen patents both make it clear that the pumps disclosed therein are to be implanted as "shunt" pumps. In cardiac or vascular surgery, "shunt" indicates that blood is being diverted away from its normal path. The Olsen and Arnold shunt systems both involve (1) taking blood out of the left atrium or out of a major vein leading to the heart; (2) pumping the diverted blood through tubes and a pump positioned alongside the heart; and, (3) injecting the blood which has passed through the pump into the aorta. While a portion of the patient's blood is being shunted through the tubing and pump, the rest of the blood continues to flow through the normal cardiac pathway (i.e., from the left atrium, into the left ventricle, and then into the aorta).

The Arnold and Olsen patents do not state that any testing in animals or humans was ever conducted on either type of pump, and a search of the National Library of Medicine's database indicated that no reports have been published which describe any testing or use of either of those devices. This is apparently due to the fact that these shunt systems suffer from a major limitation which would probably become quickly lethal if the pump ever malfunctioned.

Specifically, a shunt system as disclosed by Arnold or Olsen et al bypasses the aortic valve. As mentioned above, blood is removed from the left atrium, it passes through the tube and pump, and it is injected into the aorta, downstream of the aortic valve. Therefore, if the shunt pumps disclosed by Arnold or Olsen were to fail, even briefly, due to a mechanical or power failure, the shunt pathway would provide a backflow path through which blood would flow from the aorta, back into the left atrium. This would be catastrophic; the ventricle would quickly begin pumping as hard as it could, in response to physiologic signals from oxygen-starved tissues in the body, but the blood would merely cycle back directly into the atrium rather than passing through the complex vasculature in the body. This would quickly generate a major cardiac overload on an already diseased or damaged ventricle, which probably would fail within a matter of minutes, leading to the rapid death of the patient. Even if the patient's ventricle were capable of supplying a large amount of "residual" function, as discussed below, failure of a shunt pump would be quickly fatal.

It might be assumed that the risk of a rapidly-lethal failure could be eliminated or minimized by simply placing a check valve somewhere in the shunt tubing or pump assembly to stop backflow. Indeed, some of the pump configurations disclosed by Olsen et al indicate check valve arrangements, such as in FIG. 2. Nevertheless, this attempt at a solution would, instead of solving the problem, merely create a different problem. If an artificial mechanical surface is left in contact with stationary blood for any substantial period of time, it greatly increases the likelihood of blood clot formation, due to complex cellular processes that arise whenever "stasis" of red blood cells occurs. If a shunt pump were to temporarily fail, and if backflow were prevented by a check valve in the shunt tubing, blood cell stasis would occur in the pump, in the "shunt" tubing, and at the check valve. As a result, clot formation would quickly become a major risk. Subsequent restarting of the pump would result in immediate expulsion of the blood clot, which would be pumped directly into the aorta. The clot would travel through the vascular system until it became lodged in the brain or other organ or limb, causing a stroke or other potentially severe or lethal consequences.

No matter how many precautions are taken during manufacturing, testing, and emplacement of a blood pump, temporary power or mechanical failures are unavoidable risks that accompany the use of any mechanical device to support or assist blood circulation. For example, as stated in a circular recently issued by the National Heart, Lung, and Blood Institute (RFP No. NHLBI-HV-92-28, Oct. 8, 1992), which invited proposals for research into "total artificial heart" (TAH) systems, "It is necessary that potential catastrophic failure mechanisms be eliminated from the TAH design. Potential failure mechanisms should result in only reduced or degraded performance which is not life-threatening and allows sufficient time for corrective action."

As evidenced by the NHLBI document, the possibility of mechanical failure cannot be completely eliminated. No matter how many safeguards are taken, mechanical or power failure is always a possibility. Therefore, as stated by the NHLBI, any satisfactory blood pumping system must be designed so that a temporary power or mechanical failure will result only in reduced performance, rather than in a catastrophe that would lead quickly to the death of the patient. Whether it will ever be possible to achieve that goal, if a total artificial heart is used, remains to be seen. Nevertheless, the relevant point is clear: the possibility of a temporary power or mechanical failure can never be totally eliminated.

Another limitation of the shunt systems disclosed by Olsen et al and by Arnold is that they are not designed to provide pulsatile flow. Since the natural heart can deliver only pulsatile flow, the vascular system has evolved in a manner that has adapted itself to pulsatile flow. Accordingly, even though comparative scientific data are not entirely conclusive, it is generally believed by most doctors that pulsatile blood flow is preferable to constant-pressure flow, which is generated by most types of rotary pumps.

However, if the shunt system described by Arnold were used in a pulsatile manner, it apparently would need to increase the resistive pressure that the left ventricle would be forced to work against. In order to provide pulsatile flow, it presumably would be necessary to operate the shunt in a manner that would create maximum instantaneous pressures during systole (i.e., during ventricular contraction and ejection), so that maximal pump pressure and maximal ventricular ejection pressure would occur at the same instant. This would allow the cyclical pumping action and any residual heart function (discussed below) to cooperate with each other in providing pulsatile flow. However, if this approach were used, cyclical pump pressure output would increase the pressure in the aorta or pulmonary artery at the exact moment when the damaged or diseased ventricle is trying hard to eject blood. The "afterload" imposed on the ventricle would be increased. This would impair ventricular contribution to total output, and it would force the ventricle to perform under more difficult conditions. Pulsatile flow was not discussed or even mentioned by Arnold, presumably because of this reason. It apparently cannot be achieved by a shunt without imposing an even greater load on an already damaged and struggling ventricle.

Still another limitation of the shunt approach is that it requires exposing blood to a relatively large artificial surface. The formation of blood clots is a major risk factor whenever prosthetic pumps are implanted in the body; if any clots form, they eventually leave the pump and are pumped into limbs or vital organs, where they block subsequent blood flow. This is a frequent source of patient injury (including strokes) and death.

Two factors contribute heavily to the danger of clotting: (1) the surface area of the artificial material which is contacted by the blood, and (2) the duration of exposure of blood cells to artificial material during each pass through a pump or shunt. The CAF pump of this invention minimizes both of those factors. By using a very short in-line flow path rather than long shunt tubes, it minimizes the surface area contacted by the blood cells flowing through the pump. In addition, the CAF pump constantly washes the pump surfaces with the maximum possible quantity of blood; all of the blood being pumped through an aorta or pulmonary artery passes through the CAF pump, since there is no alternate pathway. Washing of all of the surfaces is therefore optimized. Both of these factors minimize the risk of clot formation in the subject pump.

By contrast, in a shunt system, the shunt pathway requires the creation of a relatively long flow path, using an inlet tube to couple the pump inlet to the atrium, and a second outlet tube to couple the pump outlet to the aorta. In addition, only part of the blood passes through the shunt; the remainder passes through the natural flow path of the atrium and ventricle. Therefore, the quantity of blood washing the artificial surfaces of the shunt tubing and pump is substantially reduced. Both of these factors increase the risk of clot formation in a shunt system, compared to a CAF system implanted in the aorta or pulmonary artery.

The Nash Catheter Pump, and Trans-valve Pumps

Another type of blood pumping device, described in U.S. Pat. No. 4,919,647 (Nash 1990), involves an axle-mounted impeller blade which is surrounded by a flexible collar: both the impeller and the collar are mounted at the end of a flexible catheter. A long flexible catheter device, with the pump mounted at the end, is inserted into the aorta from a remote entry point, such as an incision below the groin which provides access into a femoral artery; the catheter then passes through the descending aorta until it reaches the ascending aorta, near the heart. The long catheter device encloses a rotating "drive wire" which is coupled to the impeller blade at one end, and which emerges from the exposed end of the catheter, near the patient's groin, at the other end. When the exposed end of the drive wire is mechanically rotated, using a device located outside the patient's body, it conveys the rotational force through the length of the catheter, causing the impeller to spin at high speed near the heart.

Whenever the Nash pump is being used, the catheter must be properly positioned. It will occupy the entire length of the patient's ascending and descending aortas, and it must emerge through the skin. Therefore, this system is not really a surgically implantable pump. It may be useful as a catheter tool to assist during surgery or to provide temporary bridging support to help a patient survive a crisis, but it is not suited for any type of long-term use, since the catheter components (and possibly the collar as well) positioned in the artery would be likely to cause or aggravate clot formation.

A number of other blood pumping devices can be classified as "trans-valve" pumps. One example is described in U.S. Pat. No. 4,906,229 (Wampler 1990). When in use, trans-valve pumps are placed in a position which occupies (and blocks the action of) an aortic or pulmonary valve. These pumps are sufficiently slender to allow them to be pushed through the opening (the annulus) of an aortic or pulmonary valve, without damaging the "cusps" of the valve (i.e., the flexible tissue flaps that open to allow blood ejection during systole and then close to backflow during diastole). The cusps in aortic and pulmonary valves are not muscular, and do not respond to nerve impulses; instead, they are passive tissues which respond solely to fluid pressures from either side of the valve. Therefore, it is possible to insert a tubular pump through an aortic or pulmonary valve, blocking the normal motion of the cusps, without damaging the cusps.

The surgical method disclosed herein does not involve trans-valve placement of a pump. Instead, it relates to implanting a pump downstream of an aortic or pulmonary valve, leaving the valve intact and unimpeded and allowing valve activity to continue normally while the pump is operating.

Residual Cardiac Functioning

An important factor that needs to be considered in the design and use of implantable blood pumps is "residual cardiac function," which is present in the overwhelming majority of patients who would be candidates for mechanical circulatory assistance. The patient's heart is still present and still beating, even though, in patients who need mechanical pumping assistance, its output is not adequate for the patient's needs. In many patients, residual cardiac functioning often approaches the level of adequacy required to support the body, as evidenced by the fact that the patient is still alive when implantation of an artificial pump must be considered and decided. If cardiac function drops to a level of severe inadequacy, death quickly becomes imminent, and the need for immediate intervention to avert death becomes acute.

In the great majority of cases, it is highly advantageous to allow the natural heart, no matter how badly damaged or diseased it may be, to continue contributing to the required cardiac output whenever possible. This points away from the use of total cardiac replacements and suggests the use of "assist" devices whenever possible. However, the use of assist devices also poses a very difficult problem: in patients suffering from severe heart disease, temporary or intermittent crises often require artificial pumps to provide "bridging" support which is sufficient to sustain the entire body for limited periods of time, such as in the hours or days following a heart attack or cardiac arrest, or during periods of severe tachycardia or fibrillation.

Accordingly, the Applicant's goal during development of the described method of pump implantation and use and of the CAF pump itself, was to design a method and a device which could cover a wide spectrum of requirements, by providing two different and distinct functions. First, an ideal cardiac pumping device should be able to provide "total" or "complete" pumping support which can keep the patient alive for brief or even prolonged periods, if the patient's heart suffers from a period of total failure or severe inadequacy. Second, in addition to being able to provide total pumping support for the body during brief periods, the pump should also be able to provide a limited "assist" function. It should be able to interact with a beating heart in a cooperative manner, with minimal disruption of the blood flow generated by the natural heartbeat. If a ventricle is still functional and able to contribute to cardiac output, as is the case in the overwhelming majority of clinical applications, then the pump will assist or augment the residual cardiac output. This allows it to take advantage of the natural, non-hemolytic pumping action of the heart to the fullest extent possible; it minimizes red blood cell lysis, it reduces mechanical stress on the pump, and it allows longer pump life and longer battery life.

As discussed below, the method of pump implantation disclosed herein accomplishes all of these goals.

Accordingly, one object of this invention is to disclose a method of surgically emplacing a blood-pumping device directly in the pathway of an ascending aorta or pulmonary artery.

Another object of this invention is to disclose a method of surgically emplacing a blood-pumping device in an aorta or pulmonary artery, wherein the pump has a design that allows it to augment residual cardiac functioning in a minimal fashion when appropriate, wherein the pump can also supply blood to the entire body during periods of crisis when the patient's cardiac function becomes severely or totally inadequate.

Another object of this invention is to disclose a method of surgically emplacing a blood-pumping device in an aorta or pulmonary artery in a manner that can provide pulsatile flow while reducing the aortic or pulmonary artery pressure which the ventricle must work against during the systolic phase of each heartbeat.

Another object of this invention is to disclose a central-axial-flow (CAF) blood-pumping device which can be safely implanted into a patient in need of cardiac assistance or replacement, and which minimizes blood-contacting artificial surfaces, blood cell stasis, and lysis of blood cells.

Another object of this invention is to provide a rotary pump which provides a flow path that is as straight as possible and which is aligned with the normal flow of blood through an artery. This will minimize the shear forces, turbulence, and blood cell damage caused by the rapid acceleration and deceleration that occur within centrifugal pumps that require rapid changes in the direction of blood flow.

Another object of this invention is to provide a rotary pump having peripherally located vanes which induce blood flow through an open channel passing through the center of the pump, resulting in less cell-to-vane contact than rotary pumps containing vanes or blades which extend from a central axis across the entire conduit area.

Another object of this invention is to provide a rotary pump having peripherally located vanes which eliminate the narrow gap areas between the outer tips of axle-mounted blades and the walls of the flow conduit, and which eliminate the high levels of turbulence and shear forces in such gaps, which are one of the major sources of hemolysis in rotary blood pumps of the prior art.

These and other objects of the invention will become clear from the following description and accompanying figures.

SUMMARY OF THE INVENTION

This invention relates to a method of surgically implanting a blood pump into the ascending aorta or pulmonary artery of a patient with a diseased or damaged heart ventricle. One preferred type of pump which is well-suited for such implantation has an impeller design that generates central axial flow (CAF). After implantation of the CAF pump, blood flows through the hollowed-out rotor shaft of an electric motor. The CAF rotor shaft contains angled vanes mounted on the inner surface of the hollow shaft, extending only part of the distance toward an imaginary axis at the center of the rotor shaft. Rotation of the hollow shaft with its angled vanes pumps blood through the pumping unit. The vanes contact and impart forward motion to a portion of the blood at the periphery of the flow path, generating an outer fluid annulus which is being directly propelled by the vanes. Blood cells near the center of the cylinder are not touched by the vanes as they pass through the pump; instead, they are drawn forward by viscous flow of the surrounding annulus. In the method of this invention, the pump and motor unit is inserted downstream of an aortic or pulmonary valve which is left intact and functioning, by means such as suturing the arterial walls to short attachment cuffs at each end of the pump. After insertion, the pump lies directly in line with the artery, so that directional changes, shear forces, and artificial surfaces contacted by blood are all minimized. Unlike shunt systems, placement entirely within an aorta or pulmonary artery can provide pulsatile flow if desired, and can reduce the pressure that a damaged or diseased ventricle must pump against. In addition, the placement and design of the CAF pump allow maximal use of the residual functioning of the patient's heart and will not lead to catastrophic backflow if the pump suffers a power or mechanical failure.

BRIEF DESCRIPTION OF THE FIGURES

FIG. 3A is a view, down the central axis, of the vanes of a CAF pump, showing the outer annulus where blood cells contact the vanes, and the open central channel where blood cells do not contact the vanes.

FIG. 3B is a view along the axis of a prior art rotary pump having blades mounted on a center axle, showing the narrow gaps between the blade tips and the conduit walls, which are the sites of very high shear stresses.

FIG. 4 shows an example of seals and bearings which provide low-friction sealed interfaces between the stator and rotor.

FIG. 5 depicts a pump implanted in an ascending aorta, downstream of the aortic valve which has been left intact and functioning, and downstream of the coronary artery orifices.

DESCRIPTION OF THE PREFERRED EMBODIMENTS

Figure 1:
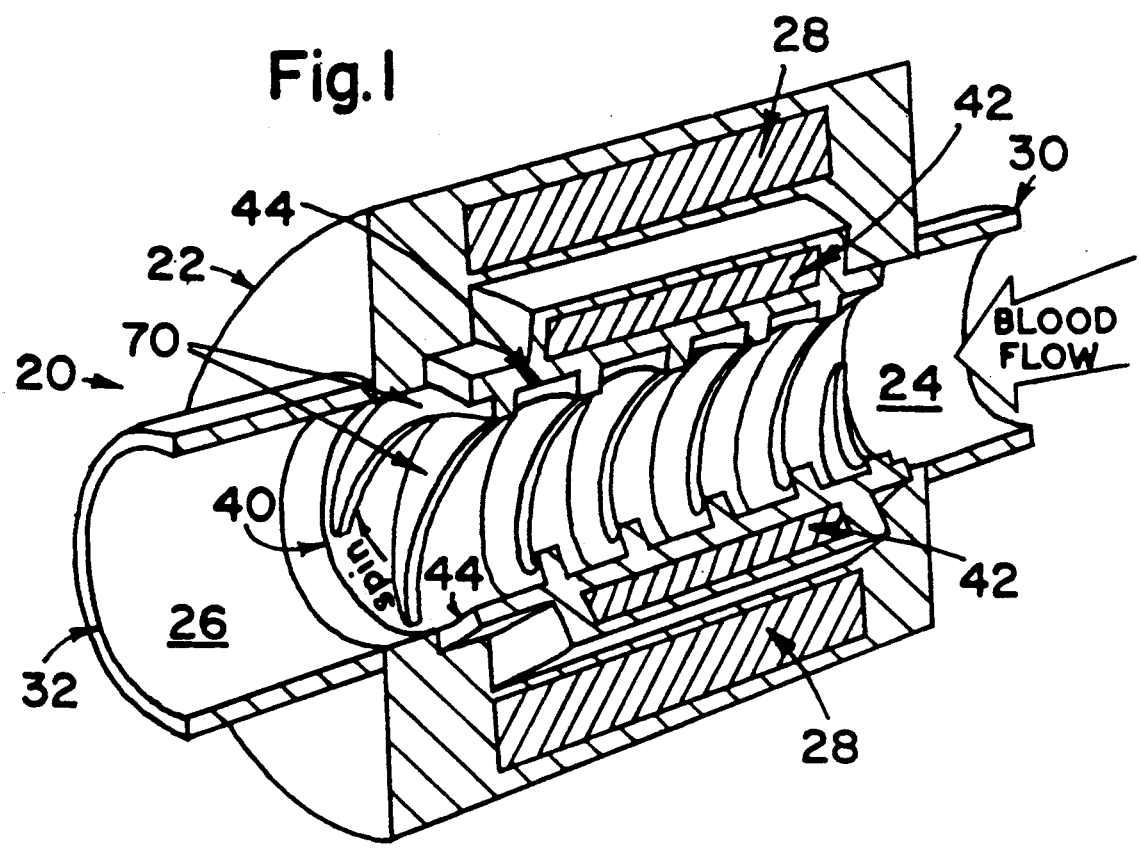
FIG. 1 is an oblique cross-sectional cutaway view of a surgically implantable central axial flow (CAF) pumping unit of this invention, showing a plurality of relatively short vanes mounted on the inside surface of a hollow rotor shaft.

Referring to the drawings by reference numbers, item 20 in FIG. 1 refers to a surgically implantable electric pump according to the subject invention, shown in a cross-sectional cutaway view. Pump 20 has dimensions which render it suitable for surgical implantation to assist in pumping blood; in general, this requires the housing 22 to be about 5 cm or less in diameter, and about 8 cm or less in length between inlet end 24 and outlet end 26.

Pump 20, shown in the illustrations, contains a stator and a rotor, which are the basic components of any conventional electric motor. As implied by their names, the rotor rotates when the motor is operated, and the stator remains stationery within the motor housing. All terms herein which refer to stationary or rotating use the patient's body as a fixed frame of reference.

The stator housing must be securely affixed to an ascending aorta or pulmonary artery. This can be done in any of several manners. For example, stator housing 22, as illustrated, is affixed to vascular attachment cuffs 30 (at inlet end 24) and 32 (at outlet end 26). After insertion into an aorta or pulmonary artery, the attachment cuffs 30 and 32 should be relatively short (such as about 2 cm or less each) so that blood cell exposure to artificial surfaces is minimized. The vascular attachment cuffs can be cuffs made of a soft and flexible material for suturing, such as double velour knitted polyester, which is sold under trademarks such as Dacron by companies such as DuPont (Wilmington, Del.) and Dow Corning (Midland, Mich.). This material encourages rapid ingrowth of endothelial cells, which provides long-term hemocompatibility. It is resistant to blood leakage but is pliant enough to allow easy passage of needles for end-to-end suturing to vascular structures such as the aorta and pulmonary artery. If suturing is used as the attachment means, it should be done with a non-absorbable monofilament such as 3-0 polypropylene.

Alternately, any other suitable type of vascular attachment device can be used, either presently known or hereafter discovered, provided that it satisfies the functional and durability requirements of the invention. Vascular attachment techniques which are currently being used or studied include clamps, biocompatible glues, collagenous or other matrices which promote cell growth, and laser-catalyzed welding or fusing of tissues or cells to synthetic objects.

In addition, it is possible to insert certain types of pumps entirely within an ascending aorta or pulmonary artery. This can be done by means such as making a longitudinal incision in an arterial wall, inserting the pump through the incision, securing it in posiiton by means such as placing sutures through the arterial wall or by using circumferential clamps to slightly constrict the arterial walls so they will conform to accomodating grooves around the pump exterior, and reclosing the arterial wall around the implanted pump.

If desired, blood pumps having the CAF design as disclosed herein can be manufactured with long attachment tubes (such as 30 cm or more) at each end. This would give surgeons the option of using such pumps as short-term shunts if desired. Although this is not the preferred mode of implantation, the impeller design disclosed herein might be preferable to the impeller designs currently in use in blood pumps, in several respects, and there is a need for shunt pumps in certain situations, particularly in short-term bridging situations. If manufactured in that manner, the long attachment tubes could easily be cut to an appropriate length for any desired use. If desired, one method of using a CAF as a temporary shunt to help a patient stabilize and recover after heart surgery would involve leaving the CAF pump outside the body, so that the exposed tubes can be immediately clamped shut if a power or mechanical failure occurs. This would minimize the risk of catastrophic backflow if the pump or power supply fails.

Stator housing 22 encloses a set of torque-generating components 28 positioned around the circumference of the housing. These torque-generating components can be either (1) stator windings made of conductive wire, which will generate an electromagnetic field when current passes through the wires, or (2) solid magnets, either in metallic form or in a ceramic matrix. Neither the stator housing 22 nor the stator windings 28 rotate; they both remain stationary after implantation.

The stator housing 22 and stator windings 28 surround rotor assembly 40, which rotates during operation of the pump. Rotor 40 contains a second set of torque-generating components 42 (also called rotor conductors 42), which can be windings, magnets, or salient conductors, depending on the type of motor used. These interact with stator component 28 to cause rotation of rotor 40 when electrical current is passed through the motor. Although rotation of rotor 40 will be in a single direction, pulsatile flow can be provided, if desired, by cyclic alteration of pump speed, as discussed below.

Smooth and vibration-free rotation is ensured by means of seals and bearing assemblies, such as shown in FIG. 4, which provide low-friction interfaces between the stator housing 22 and rotor 40. Suitable bearings and mechanical seals (which are placed between moving surfaces, as distinct from packing seals which are placed between stationary surfaces) have been developed for other types of rotary blood pumps used in the prior art. In FIG. 4, inlet seal 50 is a molded ring that can be made of an elastomer, a slightly yielding material such as polytetrafluoroethylene (Teflon TM), or a highly polished metal which can provide an extremely smooth interface. It can be provided with any desired cross-sectional shape, such as the L-shaped configuration shown in FIG. 4, which has a main body and a rim 51. Rim 51 fits into a groove 52, which is positioned either in stator housing 22 (as shown) or in rotor 40 if desired. The exposed surface 53 of seal 50 preferably should be flat, to provide a smooth juncture that includes the seal surface 53, inner surface 54 of stator housing 22, and inner surface 44 of rotor 40. This smooth juncture will minimize shear and stasis.

Inlet bearing 60, shown in FIG. 4, will be required to handle radial loads; a similar radial bearing should be provided near the outlet end. If inlet bearing 60 cannot handle the axial load (which will be equal to the pumping force exerted on the fluid), an additional bearing (often called a thrust bearing) can be provided at the inlet end. In FIG. 4, inlet bearing 60 uses ball bearings 62, which are constrained in a holding structure (commonly called a race) comprising inner ring 64 and outer ring 66. The preferred bearing type for inlet bearing 60 will depend on pump diameter and rotation rate; sleeve bearings are often preferred for motors designed to rotate at relatively low speeds, while ball bearings are preferred for units designed to rotate at high speeds.

Rotor assembly 40 has an overall shape which can be generally described as a hollowed-out cylinder. Rotor conductors 42 are positioned around the outer circumference of rotor 40, in close proximity to stator conductors 28. As in any conventional motor, electromagnetic fields are generated when electrical current is passed through windings, which can be provided as either stator windings 28 or rotor conductors 42. These current-controlled electromagnetic fields drive the rotor.

Suitable voltage is provided to the pump by means of wires 230 which are connected to a battery device 232, as shown in FIG. 5. Unlike the temporary assist device described in U.S. Pat. No. 4,919,647 (Nash 1990), which contains an impeller mounted on the end of a catheter that must remain inside the aorta to drive the impeller, the wires which supply power to the pump will be positioned outside the aorta and will not contact blood flowing through the aorta.

Various winding arrangements, commutator arrangements, and electronic control circuits are known in the art of electric motors for ensuring that the electromagnetic fields rotate around the circumference of the stator (or, if windings are inside the rotor, for ensuring that the current passing through the windings is reversed as soon as the rotor travels a short distance). These arrangements ensure that the rotor continues to rotate whenever current is applied to the motor.

The motor components described above can be provided by conventional components that are well known to those who specialize in electric motors. The foregoing merely describes various conventional electric motor arrangements, with the primary difference being that the torque-generating components are positioned around the outside of a hollow cylinder rather than around a solid shaft in the center.

An important aspect of the CAF pump described herein involves the arrangement of a plurality of rotor vanes 70. Each vane 70 is affixed along its base 72 to the interior surface 44 of the hollow cylindrical rotor 40. Because of the angled orientation of vanes 70, rotation of the rotor 40 in the direction shown in FIG. 1 will cause blood to be pumped through the pumping unit 20 in the direction shown by the axial arrow.

Figure 2:
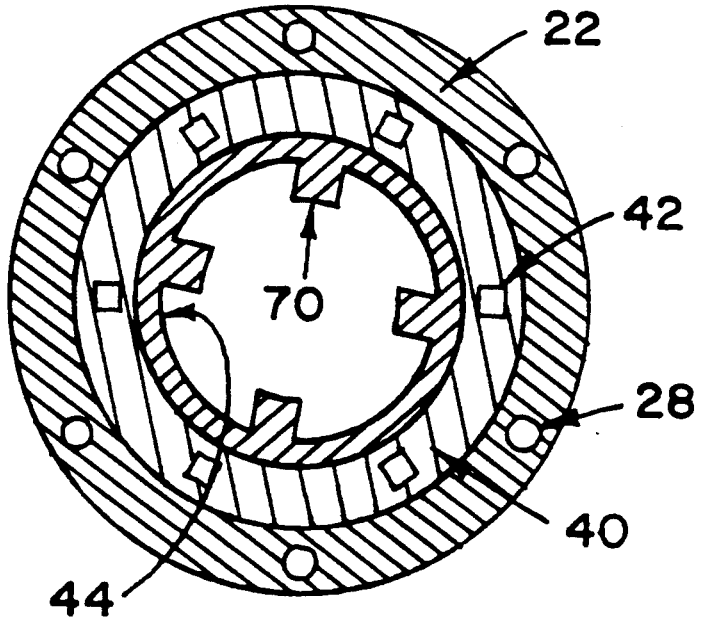
FIG. 2 is a cross-sectional view of a CAF pump seen along the longitudinal axis, looking through the central pumping chamber, showing various elements of the stator and rotor.

Each vane 70 extends in an inward direction, toward the center axis of the rotor 40, as shown in FIG. 1. However, as shown in FIGS. 1, 2, and 3A, the vanes 70 extend only part of the distance toward the imaginary center axis. This effectively generates two different pumping zones inside the pump: an outer annulus 80, and a central zone 82, as indicated by callout numbers in FIG. 3A. In the outer annulus 80, fluid occupies the troughs between the vanes 70, and the surfaces of the vanes will directly contact and impart forward motion to blood cells and serum as the rotor spins. By contrast, in central zone 82, blood cells are not directly touched by the vanes as the cells pass through the pump. Instead of being subjected to direct contact with the vanes, blood cells and serum in the central zone 82 are drawn and pushed forward solely by viscous fluid forces, due to the interface between the central zone 82 and the outer fluid annulus 80. This arrangement of rotor vanes therefore results in "central" axial flow, in contrast to prior art axial pumps which have impeller blades mounted on center axes, as shown in FIG. 3B, which generate "peripheral" blood flow. FIG. 3B depicts (in simplified form) a prior art pump assembly 90 having a conventional center-mounted axle 92 with blades 94 affixed to axle 92 and extending outwardly. The outer edges 96 of the blades approach rather closely to the inner surface of cylindrical conduit 98, leaving only narrow gaps 99 between the blade edges 96 and the conduit 98. As described in the Background section, these narrow gaps 99 are the sites of very high levels of shear stress in conventional axial pumps.

Shearing forces are important, because high levels of shear cause hemolysis (i.e., the rupture of red blood cells). At least two types of shear are relevant in hemolysis: laminar (Newtonian) shear, and turbulent (Reynolds) shear. It should also be noted that blood cell membranes are different from other types of cell membranes. In most types of mammalian cells, the membranes are reinforced by a network of tubules inside the cell, called the cytoskeleton, which helps sustain the cells in their normal shape. However, blood cells evolved in a way which allows them to stretch and elongate; this allows them to squeeze through microscopically small capillaries. This is a highly useful adaptation in nature, but the absence of a reinforcing cytoskeleton tends to render blood cells more susceptible to rupture inside artificial pumps. Hemolysis is one of the most basic and pervasive problems in designing blood pumps, and the best way to minimize it is by minimizing shear stresses inflicted on blood cells passing through a pump.

The CAF pump, when compared to prior art axial pumps, is believed to decrease both laminar and turbulent shear, for at least two reasons:

(1) direct contact between vanes and blood cells is minimized. It occurs only in the outer annular region, as shown in FIG. 3A. Blood cells which flow through the open center region do not contact the vanes; instead, they are drawn through the pump by the viscosity of the blood being pumped by the vanes in the annular region;

(2) the very high shear forces that occur in prior art axial pumps, in the narrow gaps that exist between the outer edges of the blades and the inner surfaces of the conduit, are eliminated by the CAF design.

FIG. 5 depicts a pump 200, such as the CAF pump, which has been implanted in the ascending aorta 210 of a patient. This was done by transsecting the aorta 210, thereby creating a first transsected end 212 and a second transsected end 214. These transsected ends are coupled by means such as by suturing to an inlet attachment cuff 202 and an outlet attachment cuff 204. In a patient with a properly functioning aortic valve 220, the pump should be inserted into the aorta downstream of the valve 220, which should be left intact and unimpeded, so that it will function normally.

FIG. 5 also shows the electrical wires 230 that couple the pump 200 to a surgically-implantable battery 232, which can be recharged trans-dermally. Unlike the blood-pumping catheter device described in U.S. Pat. No. 4,919,647 (Nash 1990), positioning of the wires outside the aorta prevents them from contacting blood within the aorta, which might cause or aggravate the formation of blood clots.

In the event of a pump failure due to mechanical or power supply problems, placement of a flow-through pump downstream of the valve will prevent the risk of catastrophic backflow; if the pump actuator mechanism is properly designed, it will also allow residual cardiac functioning to continue sustaining the patient despite the pump failure, with minimal impedance of blood flow due to the impeller or other actuator.

In patients suffering from valve defects, aortic valve 220 can be replaced, if necessary, using a conventional aortic replacement valve or any other type of aortic replacement valve which may become available in the future. Alternately, the pump 200 can be provided with a mechanical check valve attached to either its inlet or outlet end.

The pump 200 should also be positioned in the aorta downstream of coronary artery orifices 222 and 224. This will allow normal blood flow through the coronary arteries, as described below.

Figure 6:
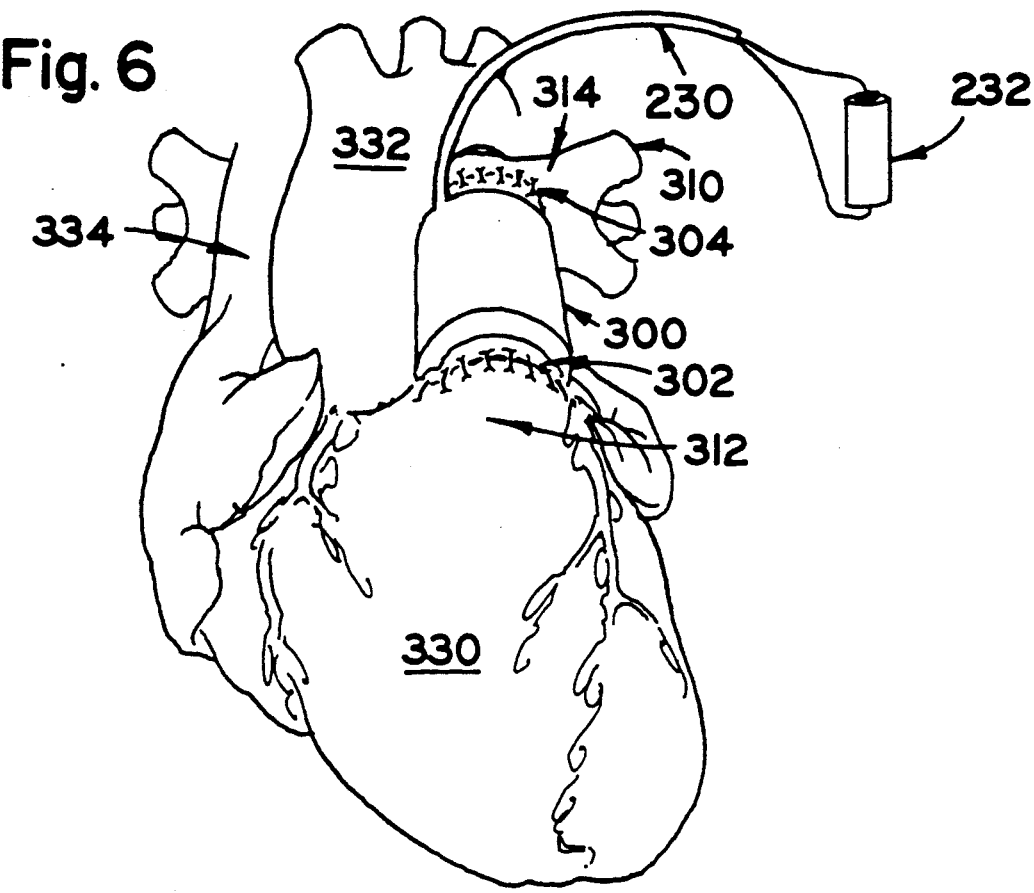
FIG. 6 depicts a pump implanted in a pulmonary artery, downstream of the pulmonary valve.

FIG. 6 depicts a pump 300 implanted in a pulmonary artery 310 by coupling inlet attachment device 302 and outlet attachment device 304 to transsected ends 312 and 314 of the pulmonary artery. FIG. 6 also shows the heart 330, aorta 332, and superior vena cava 334 for orientation. The pump should be inserted downstream of the pulmonary valve if the valve functions properly, but the native valve can be removed and replaced by an artificial valve if necessary.

Several important advantages are provided by placement of a pump such as a CAF pump directly in the aorta or pulmonary artery, downstream of the native aortic or pulmonary valve. These advantages include:

1. Prior art shunt systems normally pump blood into an aorta or pulmonary artery during systolic ejection of blood by the heart. This increases the pressure which a damaged or diseased ventricle must work against. By contrast, implantation of an entire pump (including the pump inlet) into an aorta or pulmonary artery decreases pressure at the mouth of the artery (i.e., in the region immediately adjacent to the ventricular valve). This reduction in pressure at the pump imlet helps to "unload" the ejection of blood by the ventricle. This "unloading" effect improves the efficiency of the injured heart. It augments any residual function in damaged and diseased hearts, and it can optimize the contribution of an otherwise inadequate heart to total output. In some cases, it can allow the heart to regain strength over time, by giving the heart a chance to empty completely and exercise under conditions which are not too demanding. Just as proper exercise can increase the strength and stamina of other types of muscle, it can help a heart which has been damaged by a heart attack or other trauma to regain strength, so that the natural heart function will be able to carry a greater portion of the load as days, weeks, and months go by.

2. As discussed elsewhere, the arterial mode of implantation also is ideal for providing pulsatile flow.

3. Since the aortic or pulmonary valve will be left intact, it will prevent catastrophic backflow if a mechanical or power failure occurs. This is in direct contrast to shunt systems such as the system described in U.S. Pat. No. 4,995,857 (Arnold).

4. If a CAF pump implanted into an aorta or pulmonary artery ever fails, due to power or mechanical problems, it will still allow the residual functioning of the heart to support the patient until the problem is corrected. The peripheral vanes in a CAF pump will create minimal impedance to blood flow through an inactive, non-rotating rotor. Therefore, since the patient's heart will, in most cases, continue beating normally for at least some period of time, residual cardiac capacity will be able to keep the patient alive for a substantial period of time. In most cases, the patient will quickly realize that something is wrong if the pump fails, due to sensations such as dizziness or a feeling of being out of breath for no apparent reason. Patients suffering heart trouble know what such symptoms mean, and they know what precautions to take if such symptoms begin (the patient lies down, avoids any exertion, etc.). In most patients, a number of hours or even days would be available to correct the problem. Even if a CAF pump totally fails and the rotor cylinder is completely stationary, blood can still be ejected by the heart to the rest of the body, through the large opening that passes through the middle of the rotor cylinder.

5. If implanted in an aorta or pulmonary artery, a CAF pump can cover a broad spectrum of cardiac support functions. At one end of the spectrum, it can support the entire body during periods of crisis, such as periods, of severe tachycardia or fibrillation. At the other end of the spectrum, it can be operated on a minimal support basis when the heart is functioning normally, thereby conserving battery power, using the natural cardiac functions to the maximum possible extent, and minimizing trauma and damage to blood cells.

6. The CAF pump, if implanted directly into an aorta or pulmonary artery, minimizes the area of artificial material which is contacted by blood cells. Relatively long inlet and outlet tubes, which are used by shunt systems in the prior art, can be replaced in this invention by short attachment cuffs. In addition, a shunt system handles only part of blood which must be pumped to the body or lungs. By ocntrast, a CAF pump as disclosed herein provides maximal flow rates through the pump; all of the blood which passes through a ventricle passes through the CAF pump. This decreases the contact or dwell time of blood cells inside the pump, and it increases the "washing" activity of the blood flow, which further reduces the likelihood of blood cell stasis and lysis. Both of these factors minimize the risk of blood clot formation in a CAF pump compared to prior art shunt systems.

DESIGN VARIABLES IN CAF PUMPS

Figure 7:
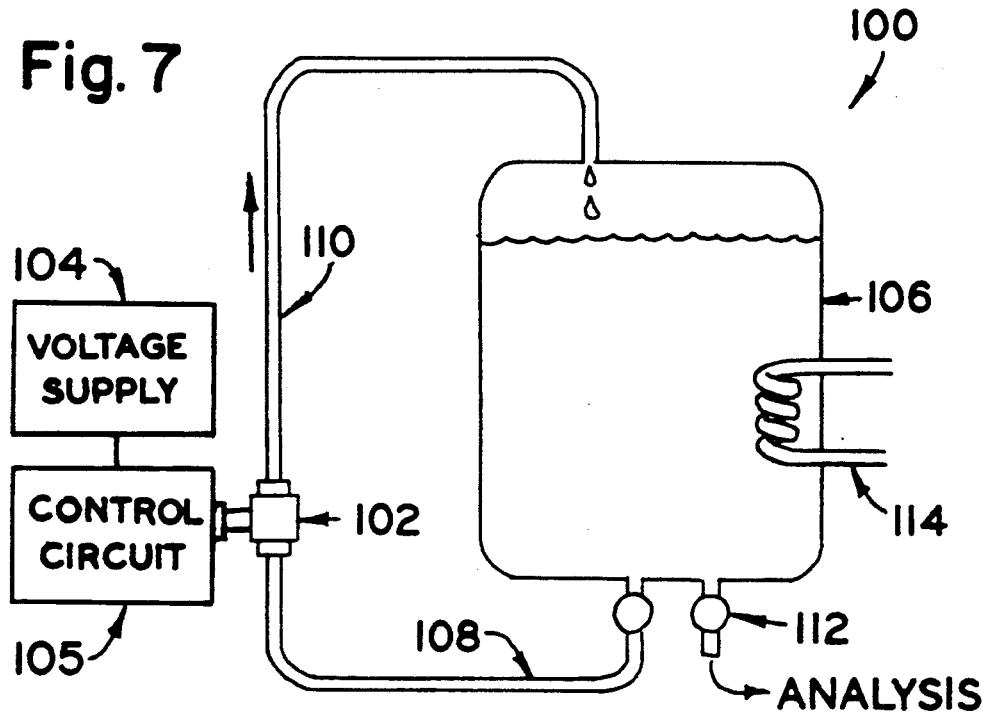
FIG. 7 depicts a pump and reservoir system that can be used to optimize vane designs for particular applications.

A number of variables described below will require evaluation to optimize the design of this pump. However, any optimization work described herein can be carried out using no more than routine experimentation, using an ex vivo test system as shown in FIG. 7.

Pump design variables which can be altered at will and tested to assess their effect on pumping efficiency and blood cell damage include the following:

1. The Height of the Vanes

To reduce turbulence at the inflow and outflow points, the internal diameter of the hollow rotor cylinder 52 should approximate the internal diameter of the patient's aorta (which varies substantially among different patients; in small children, the internal diameter of the aorta is roughly 1 cm, while in adults it is typically about 2-3 cm). If the internal diameter (ID) of a rotor cylinder is 2 cm, then the radius is 1 cm and the cross-sectional area of the cylinder is about 3.14 $cm^2$. If each vane has a height of 0.4 cm (i.e., if each vane extends 0.4 cm from the inner surface of rotor cylinder, toward the center axis of the cylinder), then the center zone, where direct contact with the vanes does not occur, will have a diameter of 1.2 cm and an area of about 1.13 $cm^2$, which is slightly more than ⅓ of the cross-sectional area of the entire cylinder. The outer annulus will occupy the other ⅔ of the cylindrical area, about 2.01 $cm^2$.

The vanes occupy a significant fraction of the area of the outer annulus, due to their thickness. For example, if the vanes occupy ¼ of the volume of the outer annulus, and the vane height is 0.4 cm in a cylinder having a 2 cm internal diameter, then the area of the center zone will remain at 1.13 $cm^2$, while the area of the outer annulus will be reduced (by the vane thickness) from 2.01 $cm^2$ to about 1.5 $cm^2$. In this situation, the center portion would occupy about 43% of the volume of the pumping cylinder.

The ratio of the central vs. annular areas can be adjusted by increasing or decreasing the height or thickness of the vanes.

2. Vanes with Varying Heights and Shapes

There are several methods of providing vanes having varying heights and shapes. In the first method, relatively tall vanes can be alternated with relatively short vanes. For example, vanes having a height of about 4 to about 8 mm can be alternated with vanes having a height of 2 or 3 mm.

In the second method, a single vane can have a relatively short height (such as about 1 or 2 mm) near the inlet end of the pump, and the height of the vane can increase gradually along the length of the vane, to about 4 to 8 mm at the outlet end.

As another alternative, vanes can be short at the inlet end, increase to a maximum height at a midpoint in the rotor shaft, and then decrease again before reaching the outlet end. Vane height may be varied between the inflow and outflow ends using linear, logarithmic, or any other smooth gradations, including rounded or sloped ends.

These various arrangements involving vane heights and shapes can be evaluated to assess their effects on pumping efficiencies, generation of turbulent and laminar shear, and blood cell lysis.

3. The Number of Vanes, and the Distances between the Vanes

It is believed that the preferred number of vanes is likely to range between three and eight; however, any number can be tested (for example, as few as two vanes, and as many as twelve, can be tested). Whether such tests are indicated will depend on whether the data gathered from initial tests indicate that the optimal number might lie outside the initial range of three to eight.

The current design uses equidistant spacing between adjacent vanes. If desired, this parameter can also be tested.

4. The Pitch and Cross-sectional Shape of the Vanes

The pitch (angle) of the vanes can be measured relative to either (1) an imaginary central axis of the pump (axial), or (2) an imaginary cross-sectional plane which is perpendicular to the central axis (radial). Initial design utilizes a range of about 30° to 60° (measured either axially or radially). This is based upon modeling work and testing that has previously been reported for axle-mounted impellers (Qian 1989 and Qian 1990a). Pitches which vary from those angles will be tested, with both linear and logarithmic application.

The cross-sectional shape of the vanes is also an important factor. Leading edges preferably should be relatively narrow yet somewhat rounded, so they can move through the blood smoothly and minimize the number of cells that are directly impacted. Trailing edges should be tapered to minimize turbulence in their wake. Abrupt transitions and sharp corners should be avoided, to minimize turbulence.

Qian 1989 and Qian 1990a offer a useful example of vane design and testing. Even though those two articles relate solely to impeller blades which were mounted on center-axles and which extended outwardly, they describe the types of tests and experimental data that are gathered during testing of various vane shapes, and they discuss the equations and algorithms that can be used to develop computer models of vane designs.

5. Pre-rotor and Post-rotor Flow Guides

If desired, one or more stationary angled flow guides can be placed at the inlet and/or outlet of a CAF pump. For example, a set of helical blades, which can be mounted peripherally (on the inside surface of the stator housing) or across the entire entry face of rotor, can be placed inside the stator housing at the pump inlet, in order to impart a swirling motion to the blood that is being drawn into the rotor inlet. This can reduce the abruptness of the transition from linear flow (prior to the pump inlet) to the swirling motion generated inside the pump.

6. The Speed of the Rotor

Pump requirements will vary, depending upon the specifics of the patient. In a normal healthy adult, blood flow depends primarily on body surface area (2.5 liters per minute per square meter of body surface area is typical), blood pressure (which in most adults has a mean value of about 60 to 75 millimeters of mercury (mm Hg)), and on transient states of bodily activity and exertion. The speed of the rotor (which can be constant or pulsatile, as discussed below) is an important factor that will interact with various other factors, such as the internal diameter of a pump, the height and pitch of the vanes, and the amount of pressure resistance in the system, to control the volume of blood that will pass through a pump during a given period of time.

The numerical ranges discussed above or indicated by publications describing other types of ventricular assist devices (VAD's) suggest useful ranges for initial testing. Obviously, if the results of any of these tests indicate that a combination of good pumping efficiency and low blood cell damage is still increasing at or near a boundary of any suggested range, the relevant tests can be extended beyond the initially selected range limits.

It is possible and perhaps even likely that various different designs will prove to be optimal for different uses. For example, one particular vane design might be preferred for use in neonates and children; a second vane design might be preferred for adults having normal blood pressure, in aortic implantations; a third vane design might be preferable for aortic implantation in patients who suffer from high blood pressure, and still another design might be preferred for insertion into pulmonary arteries rather than aortas.

PULSATILE VS. CONSTANT-SPEED OPERATION

As mentioned in the Background section, since the vascular system has evolved in a manner adapted to pulsatile flow, it is generally presumed by many doctors that pulsatile flow is preferable to constant-pressure flow. Accordingly, pulsatile flow can be generated by varying the speed of rotation of the rotor (or by other appropriate control of the actuator, if a non-rotary actuator is used). During systole (ventricular contraction and ejection), the rotor speed will reach a maximum level; during diastole (ventricular relaxation and expansion, during which the ventricle fills with blood), rotor speed will decrease. These cyclic changed in rotor speed can be accomplished by using appropriate control circuitry, which preferably should include an electronic monitor or pacing device to ensure that maximum rotor speed is timed to occur during the systolic phase of each heartbeat. Electronic control systems that have been used successfully with other types of implantable rotary blood pumps to generate pulsatile flow are described in articles such as Qian et al 1989, Qian 1990b, and Trinkl et al 1991. In general, it is necessary to provide an electric monitoring lead, or possibly a pacemaker, which provides a signal to the pump control system, to ensure that the speed of the pump is properly coordinated with the heartbeat cycle.

Additional factors that need to be considered in planning or evaluating pulsatile-speed or constant-speed operation of an arterial pump relate to (1) the closure of aortic or pulmonary valves, and (2) the flow of blood through coronary arteries.

In general, pulsatile-speed operation of a CAF pump which slows down substantially during diastole will not affect either closure of an aortic or pulmonary valve, or diastolic flow through coronary arteries. In a healthy person, the coronary arteries fill during diastole, when the ventricles expands to take in more blood. The resistive pressure of the vascular system, and the resilience of non-hardened arteries, interact to generate substantial pressure at the outlet side of the aortic valve during diastole. This backflow pressure, which causes the aortic valve to close, also causes the coronary arteries to become filled with fresh blood during each diastolic cycle. Accordingly, in an ascending aorta, the CAF pump should be positioned downstream of the coronary artery orifices. If the pump is operated in pulsatile mode, then the slowing of the rotor speed during each diastolic phase should prevent any interference of the pump with coronary artery flow.

By contrast, constant-speed operation of arterially placed pumps raises questions as to whether the pump might interfere with either valve closure, or flow through coronary arteries. Since a constant-speed pump would be constantly trying to pull blood away from the valve, it might impede the ability of back-pressure to close the valve or to provide adequate flow through the coronary arteries.

One potentially significant factor suggests that constant-speed operation of a CAF pump, if it is used, would still allow proper valve closure and coronary blood flow, so long as the pump is properly sized for the patient. In general, a suitable pressure head at the inlet end of a pump substantially increases the pumping efficiency and output volume of the pump, while a drop in pressure head at the pump inlet leads to a major drop in the efficiency of the pumping activity. Therefore, if a CAF pump implanted into an artery is operated in a constant-speed mode, then during systole, when the native heart is ejecting blood into the inlet of a pump which is spinning at a constant rate, the ventricle and rotor will work together to enhance the ejection of the heart. This will generate pulsatile flow to the body, due to the pulsatile action of the heart, even when the pump is being operated at constant speed. However, when systolic ejection ends and the ventricle expands to take in more blood from the atrium, the pressure head supplying the pump inlet will decrease sharply, and the efficiency of the pump will drop off sharply. Therefore, if the rotor and vane dimensions and the rotational speed of the rotor are properly designed to allow constant-speed operation, it appears likely that the large central flow channel passing through a CAF pump will allow sufficient blood to flow back through the flow channel to ensure proper closure of the aortic valve and normal filling of the coronary arteries.

If constant-speed operation is desired (which seems unlikely, in view of these concerns and in view of the perceived preferability of pulsatile flow from from a physiologic perspective), these concerns about valve closure and coronary flow will need to be evaluated by experimentation over a range of support requirements that are likely to be encountered in patients with ventricular disease or damage. As noted in the Background section, one of the most significant advantages of the CAF pump and the implantation method disclosed herein is that this pump and method can be used to provide a broad range of support requirements, from minimal support when a patient's heart is functioning properly, to total or near-total support if a crisis occurs, such as when a heart begins to fibrillate. Such experimentation may reveal that (1) pulsatile-speed operation of the pump will always be preferable, or that (2) constant-speed operation can be adequate during periods when the heart is functioning normally, but pulsatile-speed flow becomes necessary if the heart encounters a crisis. Regardless of the outcome of such experimentation, it appears that a solution can be provided, whenever necessary, by using pulsatile-speed rotation of the pump rotor. This can be provided and controlled electronically, as described above.

EX VIVO TESTING OF PUMPS

All of the foregoing variables can be evaluated and optimized using no more than routine experimentation, using a pump and reservoir system 100 as shown in FIG. 7. System 100 includes: (a) a CAF pump unit 102, as disclosed above, which is driven by a voltage supply 104; (b) an electronic control circuit 105, which preferably can interact with voltage supply 104 and pump 102 to provide pulsatile flow; (c) a reservoir 106; (d) an inlet conduit 108 which carries blood from reservoir 106 to the inlet of pump 102; (e) an outlet conduit 110 which carries blood from the outlet of pump 102 back to the reservoir 106; and (f) at least one sampling port 112.

Reservoir system 100 should also be provided with a heating element 114, which can be an electrical resistance coil or a heat exchanger tube which carries a heated liquid, to maintain the blood at 37° C. If desired, a membrane oxygenator can be provided to sustain an oxygen content that simulates the oxygen content of blood which passes through the aorta. These components can be provided by using the reservoir, heat exchanger, and oxygenator components (without the pump) from a standard cardiopulmonary bypass machine.

If desired, the system can be equipped with a filter to remove extraneous particles and cell aggregates; however, any filtering or other mechanical processing preferably should be minimized during actual pump testing, to reduce any uncertainty about whether such processing might contribute to (or mask the effects of) hemolysis. Reservoir system 100 should also ensure that the pump must work against a pressure differential that simulates vascular resistance in the body. This can be accomplished by standard mechanical resistance devices (often called chokes), or possibly by forcing the pump to lift blood a certain height in the outlet conduit 110 before the blood returns to the reservoir 106 (provided that siphoning effects are avoided). Mechanical devices with variable pressure drops can be used to test vane designs in pumps intended for patients with high blood pressure.

Reservoir system 100 will repeatedly cycle blood (such as blood donated by human volunteers, which can be treated with an anticoagulant during testing if desired) through test pump 102. During each test, the pump 102 will use a rotor assembly that is being evaluated to assess the effects of a particular vane design involving a combination of height, number, pitch, and other factors described above. Since these testing pumps will be designed solely to evaluate rotor design, the stator assembly can be provided with a closure device that will allow rapid and easy insertion and removal of rotor cylinders having different vane structures.

The test pump will be run for a desired period, such as several hours for pumps designed solely for short-term support, up to several weeks (or more, if new blood is periodically added) for pumps designed for permanent emplacement. Comparative testing in this manner can provide highly useful data to compare and optimize different types of vane designs.

During an ex vivo test using an artificial system to evaluate pump performance and blood cell hemolysis, the pumping efficiency of the rotor can be evaluated at (1) a constant speed; (2) varying speeds; (3) one or more desired flow rates. Such tests can use a constant resisting pressure, such as a mean pressure of 60-75 mm Hg, which is a typical vascular pressure that a left ventricle must work against, or 16-24 mm Hg to simulate pulmonary circulation. The data that should be recorded and evaluated in assessing pumping efficiency include the rate of blood flow through the pump (in volume per time, such as liters per minute) and the amount of electrical power (in watts or milliwatts) required to run the pump. At the end of a test, or at any point during a test, the blood circulating through the system can be sampled and evaluated by any of several tests to assess the amount of damage being inflicted on blood cells by the pump.

The most widely used test for blood cell damage is the "Index of Hemolysis" (IH) test. In this test, the concentration of hemoglobin which has been released by lysed cells during a known test period is measured by suitable means, such as spectrophotometrically. This concentration is usually expressed in terms such as grams of hemoglobin per deciliter of blood (g/dL). The g/dL value can be divided by the quantity of fluid which was pumped during the test, to provide a g/dL/hour or g/dL/liter rate of hemoglobin release. A high IH level indicates high levels of red blood cell rupture. The IH test is discussed in articles such as Qian 1989a.

Vane designs that have been optimized in this manner, using ex vivo systems, can be further tested by in vivo tests, using animals such as dogs or cows.

Implantation of Other Types of Pumps in Ascending Aortas or Pulmonary Arteries

The method of this invention discloses a number of advantages which can be achieved by implanting a pump having a suitable flow path into a transsected ventricular outflow artery. Although the CAF pump described herein discloses a preferred type of pump for use in this method, it is not the only type of pump which can be implanted using the method and positioning described herein. For example, the single-vane configuration described in U.S. Pat. No. 4,995,857 (Arnold, 1991) or the helifoil vane used in the Haemopump (sold by Nimbus) might be adaptable to this method of implantation; however, the dimensions of those vane types would need to be optimized in order to reduce the impedance to blood flow that would arise if the pump ever suffered a mechanical or power failure. Alternately, it may be possible to develop a pump having an entirely different type of actuator mechanism, possibly a non-rotating actuator device, which could augment ventricular ejection when the pump and heart are functioning properly, and which could be designed to cause minimal impedance to blood flow if the pump fails but the ventricle continues to eject blood in the normal manner.

In general terms, the pumps suitable for use in the method described herein can be regarded as having the following essential components: (1) a housing with a flow path passing therethrough, with an opening at each end of the housing for inflow and outflow of blood, which can be either inserted inside a ventricular outflow artery or coupled to the ends of a transsected artery; (2) a pumping actuator (such as a rotatable rotor having suitable angled vanes) mounted within said housing; and (3) electrical means for driving the actuator in a manner that causes the pump to augment the pumping of blood ejected by the ventricle. In order to provide safe operation which allows residual cardiac function to keep the patient alive for a substantial period of time, the housing and actuator must also be designed in a manner that allows blood to continue flowing through the pump due to natural ventricular ejection if the pump suffers a mechanical failure or loss of power. The CAF vane design satisfies these design goals and constraints in a highly useful manner, but it is not the only mechanical design capable of doing so, and a significant aspect of this invention rests upon the realization that various advantages can be obtained by surgically implanting a suitably designed pump directly into a ventricular outflow artery, rather than as a shunt or trans-valve pump.

It should also be noted that this invention suggests a method of providing assistance to people suffering biventricular heart failure. Two CAF or other suitable pumps can be implanted into both the aorta and the pulmonary artery, using the method disclosed herein, while the patient's damaged or diseased heart is left in place, to take advantage of any residual cardiac function. This may provide the closest approximation possible to a so-called "total artifical heart" which satisfies the goal (as set forth by the NHLBI) of avoiding catastrophic failure if either or both pumps suffer a mechanical or power failure.

Material and Component Selection

The pump housing can be composed of any suitably hard biocompatible material, such as stainless steel, various other alloys, graphite, or plastic. It can be sealed with a standard waterproof epoxy coating.

All blood-contacting surfaces should be either made of or covered with a layer of non-thrombogenic biocompatible material. Extensive work has been done on such materials, and research is actively continuing on such materials. One material which has been shown to have a good combination of biocompatibility and high strength is pyrolytic carbon, which is used to coat the housing and leaflets of various types of prosthetic heart valves, such as the St. Jude valve. It can be applied by a vapor deposition process, resulting in a layer containing about 90% carbon and 10% silicon on the surface of a graphite structure.

Implantable battery packs have been developed which can be recharged by means of a subcutaneously-implanted induction coil that interacts with a external coil worn outside the body in a belt configuration. This type of trans-dermal recharging system is described in articles such as Weiss et al 1989, and is available through companies such as Novacor.

If desired, direct current (DC) supplied by a battery can be passed through an electronic converter (usually called an inverter) to convert it from DC to alternating current (AC). Using circuitry and components that are well-known to those skilled in the art of electronic motor controls, the battery output can be electronically manipulated to regulate the speed of the motor, and to provide pulsatile flow if desired.

In addition, major progress has been made recently in developing trans-dermal electronic monitoring and control systems. Such systems can be adapted for use with the pump of this invention. For example, the surgically implanted electronic control system which governs the pump speed can include, as one of its components, a radio-frequency receiver. If a certain type of radio signal (which is encoded and/or bracketed by a specific signal sequence in order to avoid spurious activation) is received, it triggers a control function which has been programmed into an integrated circuit in the control system. This will modify the control parameters in the control system, to carry out a desired function such as altering the pump speed or pulsation cycle.

Thus, there has been shown and described a new method of surgically implanting a pump directly into an ascending aorta or pulmonary artery, and a new type of pump design which is well-suited to this method of implantation. It will be apparent to those skilled in the art that various minor changes, modifications, and other uses and applications which do not depart from the spirit and scope of the invention are possible. Such changes, if they are derived from the teachings herein and do not depart from the spirit and scope of the invention, are deemed to be covered by the invention, which is limited only by the claims that follow.

REFERENCES

DeVries, W. C., et al, "Clinical use of the total artificial heart," *New Engl J Med* 310: 273-8 (1984)

Farrar, D. J., et al, "Heterotopic prosthetic ventricles as a bridge to cardiac transplantation: A multicenter study in 29 patients," *New Engl J Med* 318:333-40 (1988)

Hogness and Antwerp, eds., *The Artificial Heart: Prototypes, Policies and Patients* (Institute of Medicine and National Academy Press, Washington, D.C., 1991)

Qian, K. X., et al, "The realization of pulsatile implantable impeller pump with low hemolysis," *Artif. Organs* 13:162-169 (1989)

Qian, K. X., "Experience in reducing the hemolysis of an impeller assist heart," *Trans. Am. Soc. Artif. Intern. Organs* 35:46-53 (1989)

Qian, K. X., "Haemodynamic approach to reducing thrombosis and haemolysis in an impeller pump," *J. Biomed. Engr.* 12:533-535 (1990a)

Qian, K. X., "New investigations of a pulsatile impeller blood pump," *Trans. Am. Soc. Artif. Intern. Organs* 36:33-35 (1990b)

Trinkl, J., et al, "Control of pulsatile rotary pumps without pressure sensors," *Trans. Am. Soc. Artif. Intern. Organs* 37:M208-210 (1991)

Weiss, W. J., et al, "In vivo performance of a transcutaneous energy transmission system . . . ,"*Trans. Am. Soc. Artif. Intern. Organs* 35:284-288 (1989)

I claim:

1. A method for assisting blood flow in a patient in need thereof, comprising the step of surgically inserting an electric pump into a ventricular outflow artery, wherein the pump is positioned in a manner which causes blood being ejected by a ventricle to flow into and through the pump, wherein the pump comprises:
   (1) a pump housing with a central axial flow path passing therethrough, with an opening at each end of the housing for inflow and outflow of blood;
   (2) an electric motor enclosed within the housing, wherein all components of the motor are arrayed within the housing in a manner that does not block blood flow through the central axial flow path, wherein the motor comprise:
   (a) a stator which is affixedly mounted within said housing and which contains a first set of electromagnetically interactive torque-generating components;
   (b) a rotor which is rotatably mountie in said hosing, wherein the rotor contains a second set of electromagnetically integrative torque-generation components which interact with the stator to cause rotation of the rotor when electrical current is passed through the motor, wherein aid second set of torque-generating components affixed in the rotor are mourned on an outside surface of an open cylindrical rotor shaft having a central flow path passing therethrough, said flow path being bounded by a circumferential inner surface of the rotor shaft; and,
   (c) rotor vanes mourned on the inner surface of the rotor shaft, said vanes having a configuration, height, and angled orientation which impart pumping force to a liquid within the central flow path of the rotor shaft when said rotor shaft is rotated.

2. The method of claim 1 wherein the pump is surgically implanted into an ascending aortic wall, downstream from an aortic valve which remains functional after surgery, and downstream from all coronary artery orifices in the aortic wall.

3. The method of claim 1 wherein the pump is surgically implanted into a pulmonary artery, downstream from a pulmonary valve which remains functional after surgery.

4. The method of claim 1 wherein the pump is surgically inserted into ventricular outflow artery by means of the following steps:
   a. transsecting the ventricular outflow artery, thereby generating two exposed transsected ends of an arterial wall; and,
   b. implanting an electrical pump between the transsected ends of the arterial wall, using arterial attachment devices coupled to each end of the pump.

5. The method of claim 1 wherein the pump is used to augment pulsatile flow of blood, by electronically controlling the rotor speed to provide maximal rotor speed during systolic ejection by the ventricle, and reduced rotor speed during diastolic expansion of the ventricle.

6. A method for assisting blood flow in a patient in need thereof, comprising the step of surgically implanting an electrically driven pumping unit having a rotary pumping mechanism into a ventricular outflow artery, wherein the rotary pumping mechanism comprises a housing with a flow path passing therethrough and a rotatable pumping vane which can be rotated under control of an electrical power system, wherein said rotary pumping mechanism has a flow path passing therethrough, said flow path being bounded by a circumferential inner surface of a tubular rotor shaft and by at least one pumping vane mounted on the inner surface of the rotor shaft, said vane having a shape and angled orientation which cause said vane to impart pumping force to a liquid within the flow path of the rotor when said rotor is rotated.

7. The method of claim 6 wherein a plurality of pumping vanes are mounted on the inner surface of the rotor shaft, and wherein the pumping vanes extend only part of the distance between the inner surface of the rotor shaft and a center axis in said rotor shaft, thereby providing an open channel for flow of blood through the rotor shaft.

8. The method of claim 6 wherein the pump is surgically implanted into an ascending aortic wall, downstream from an aortic valve which remains functional after surgery, and downstream from all coronary artery orifices in the aortic wall.

9. The method of claim 6 wherein the pump is surgically implanted into a pulmonary artery, downstream from a pulmonary valve which remains functional after surgery.

10. The method of claim 6 wherein the pump can be used to augment pulsatile flow of blood, by electronically controlling the rotor speed to provide maximal rotor speed during systolic ejection by the ventricle, and reduced rotor speed during diastolic expansion of the ventricle.

11. A method for assisting blood flow in a patient in need thereof, comprising the step of surgically inserting an electric pump into a ventricular outflow artery, wherein the pump is positioned in a manner which causes blood being ejected by a ventricle to flow into and through the pump, wherein the pump comprises:
 (1) a housing with a flow path passing therethrough, with an opening at each end of the housing for inflow and outflow of blood, wherein each end of the housing is coupled to an arterial attachment device;
 (2) pumping actuator means mounted within said housing;
 (3) electrical means for driving the pumping actuator in a manner which causes the pump to augment the pumping of blood ejected by the ventricle into the patient's vascular system;
 and wherein the pump is electrically coupled to a power supply capable of supplying a voltage suitable for driving the pumping actuator, and wherein the pump housing and actuator means are designed in a manner which allows blood to continue flowing through the pump due to natural ventricular ejection if the pump suffers a mechanical failure or loss of power.

12. The method of claim 11 wherein the pump is surgically implanted into an ascending aortic wall, downstream from an aortic valve which remains functional after surgery, and downstream from all coronary artery orifices in the aortic wall.

13. The method of claim 11 wherein the pump is surgically implanted into a pulmonary artery, downstream from a pulmonary valve which remains functional after surgery.

14. The method of claim 11 wherein the pump can be used to augment pulsatile flow of blood, by electronically controlling the actuator to provide maximal augmentation of native ventricular ejection during systole, while maintaining normal coronary artery flow.

* * * * *